US011884605B2

(12) United States Patent
Pollefeyt et al.

(10) Patent No.: US 11,884,605 B2
(45) Date of Patent: Jan. 30, 2024

(54) HYBRID CATALYSTS COMPRISING A ZEOLITE AND A MIXED METAL OXIDE COMPONENT FOR CONVERTING SYNGAS INTO $C_2$ AND $C_3$ OLEFINS

(71) Applicant: Dow Global Technologies LLC, Midland, MI (US)

(72) Inventors: Glenn Pollefeyt, Wondelgem (BE); Davy L. S. Nieskens, Terneuzen (NL); Vera P. Santos Castro, Terneuzen (NL); Alexey Kirilin, Terneuzen (NL); Adam Chojecki, Ghent (BE); David Yancey, Midland, MI (US); Andrzej Malek, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 17/253,925

(22) PCT Filed: Jun. 20, 2019

(86) PCT No.: PCT/US2019/038192
§ 371 (c)(1),
(2) Date: Dec. 18, 2020

(87) PCT Pub. No.: WO2020/005701
PCT Pub. Date: Jan. 2, 2020

(65) Prior Publication Data
US 2021/0268482 A1  Sep. 2, 2021

Related U.S. Application Data

(60) Provisional application No. 62/692,139, filed on Jun. 29, 2018.

(51) Int. Cl.
| | | |
|---|---|---|
| C07C 1/04 | (2006.01) |
| B01J 21/04 | (2006.01) |
| B01J 23/00 | (2006.01) |
| B01J 23/26 | (2006.01) |
| B01J 29/85 | (2006.01) |
| B01J 35/00 | (2006.01) |
| C10G 2/00 | (2006.01) |
| B01J 37/08 | (2006.01) |

(52) U.S. Cl.
CPC ............. *C07C 1/043* (2013.01); *B01J 21/04* (2013.01); *B01J 23/002* (2013.01); *B01J 23/26* (2013.01); *B01J 29/85* (2013.01); *B01J 35/0006* (2013.01); *B01J 37/088* (2013.01); *C10G 2/334* (2013.01); *C07C 2521/02* (2013.01); *C07C 2523/06* (2013.01); *C07C 2523/08* (2013.01); *C07C 2523/26* (2013.01); *C07C 2529/85* (2013.01)

(58) Field of Classification Search
None
See application file for complete search history.

(56) References Cited

U.S. PATENT DOCUMENTS

| 4,177,167 A * | 12/1979 | Manara ................ B01J 31/0231 |
| | | 502/506 |
| 4,472,535 A | 9/1984 | Chang et al. |
| 8,513,315 B2 | 8/2013 | Kibby |
| 10,532,961 B2 | 1/2020 | Pan et al. |
| 2008/0319245 A1 | 12/2008 | Fujimoto et al. |
| 2009/0018371 A1 | 1/2009 | Klepper et al. |
| 2014/0316177 A1* | 10/2014 | Ge .......................... B01J 29/7007 |
| | | 502/79 |
| 2018/0194700 A1* | 7/2018 | Pan .......................... B01J 23/26 |

FOREIGN PATENT DOCUMENTS

| CN | 103071528 A | 5/2013 | |
| JP | 2007181755 A | 7/2007 | |
| WO | 2010068364 A2 | 6/2010 | |
| WO | WO-2017000427 A1 * | 1/2017 | ............ B01J 23/002 |
| WO | 2017074558 A1 | 5/2017 | |
| WO | 2018119195 A1 | 6/2018 | |
| WO | 2018144840 A1 | 8/2018 | |

(Continued)

OTHER PUBLICATIONS

International Search Report and Written Opinion pertaining to PCT/US2019/038197, dated Sep. 6, 2019.
International Search Report and Written Opinion pertaining to PCT/US2019/038192, dated Aug. 28, 2019.
Jiao et al., "Selective Conversion of Syngas to Light Olefins", Science, 2016, 351, 1065-1068.
Cheng et al., "Direct and Highly Selective Conversion of Synthesis Gas to Lower Olefins: Design of a Bifunctional Catalyst Combining Methanol Synthesis and Carbon-Carbon Coupling", Angewandte Chemie Int. Ed., 2016, 55.
Liu et al., "Selective transformation of carbon dioxide into lower olefins with a bifunctional catalyst composed of ZnGa2O4 and SAPO-34", Chem. Commun., 2018, 54, 140-143.

(Continued)

*Primary Examiner* — In Suk C Bullock
*Assistant Examiner* — Alyssa L Cepluch
(74) *Attorney, Agent, or Firm* — Dinsmore & Shohl LLP

(57) ABSTRACT

A hybrid catalyst including a metal oxide catalyst component comprising chromium, zinc, and at least one additional metal selected from the group consisting of aluminum and gallium, and a microporous catalyst component that is a molecular sieve having 8-MR pore openings. The metal oxide catalyst component includes anatomic ratio of chromium:zinc (Cr:Zn) from 0.35 to 1.00, and the at least one additional metal is present in an amount from 25.0 at % to 40.0 at %. A process for preparing C2 and C3 olefins comprising: a) introducing a feed stream comprising hydrogen gas and a carbon-containing gas selected from the group consisting of carbon monoxide, carbon dioxide, and mixtures thereof into a reaction zone of a reactor; and b) converting the feed stream into a product stream comprising C2 and C3 olefins in the reaction zone in the presence of said hybrid catalyst.

18 Claims, No Drawings

(56) References Cited

FOREIGN PATENT DOCUMENTS

| WO | 2019030279 A1 | 2/2019 |
|---|---|---|
| WO | 2019074894 A1 | 4/2019 |

OTHER PUBLICATIONS

Twigg et al., "Deactivation of copper metal catalysts for methanol decomposition, methanol steam reforming and methanol synthesis", Topics in Catalysis, 2003, vol. 22, Nos. 3-4, 191-203.

Dawood et al., "Catalyse Bifonctionnelle : Hydrocondensation Du Monoxyde De Carbone Sur Cu/Zn-Mordenite", Nouveau Journal de Chimie, 1984, pp. 601-604.

Simard et al., "ZnO—C/\C/\ + ZSM-5 catalyst with very low Zn/Cr ratio for the transformation of synthesis gas to hydrocarbons", Applied Catalysis A: General, 1995, pp. 81-98.

Erena et al., "Study of Physical Mixtures of CrzOs—ZnO and ZSM-5 Catalysts for the Transformation of Syngas into Liquid Hydrocarbons", Ind. Eng. Chem. Res., 1998, pp. 1211-1219.

Li et al., "Direct conversion of syngas into hydrocarbons over a core-shell Cr—Zn@SiO2@-SAPO-34 catalyst," Chinese J. Catal., 2015, 36, 1131-1135.

Inui, T., "Highly Effective Conversion of Carbon Dioxide to Valuable Compounds on Composite Catalysts", Catalysis Today, 1996, 329-337.

Inui, T., "Rapid Catalytic Processes in Reforming of Methane and Successive Synthesis of Methanol and its Derivatives", Applied Surface Science, 1997, 26-33.

Hoflund et al., "An Efficient Catalyst for the Production of Isobutanol and Methanol from Syngas. Xi. K- and Pd-promoted Zn/Cr/Mn spinel (excess ZnO)", Catalysis Letters, 1999, 169-173.

Stiles et al., "Catalytic Conversion of Synthesis Gas to Methanol and Other Oxygenated Products", Industrial & Engineering Chemistry Research, 1991, 811-821.

Higuchi et al., "A Study for the Durability of Catalysts in Ethanol Synthesis by Hydrogenation of Carbon Dioxide", Studies in Surface Science and Catalysis, 1998, 517-520.

Tan et al., "Syntheses of Isobutane and Branched Higher Hydrocarbons from Carbon Dioxide and Hydrogen over Composite Catalysts", Industrial & Engineering Chemistry Research, 1999, 3225-3229.

Argentine Patent Application No. 20190101792 Substantive Examination Report dated Sep. 21, 2022, 3 pages.

Conversion of Synthesis Gas to Light Olefins: Impacts of Hydrogenation Activity of Methanol Synthesis Catalyst on the Hybrid Process Selectivity over Cr—Zn and Cu—ZN with SAPO-34, Alexey V. Kirilin et al., Ind. Eng. Chem. Res., vol. 56, No. 45, pp. 13393-13402 (2017).

Chinese Office Action issued by the Chinese Patent Office for related Chinese Patent Application No. 201980035355.5 dated Jan. 12, 2023 (16 total pages).

CN Office Action and Search Report, dated Jul. 17, 2023, pertaining to Chinese Patent Application No. 201980035355.5, 17 pgs.

Chinese Office Action dated Oct. 30, 2023, pertaining to CN Patent Application No. 201980035355.5, 19 pgs.

\* cited by examiner

HYBRID CATALYSTS COMPRISING A ZEOLITE AND A MIXED METAL OXIDE COMPONENT FOR CONVERTING SYNGAS INTO $C_2$ AND $C_3$ OLEFINS

CROSS REFERENCE TO RELATED APPLICATIONS

This application is a § 371 national stage entry of PCT/US2019/038192, filed Jun. 20, 2019, which claims priority to U.S. Provisional Patent Application No. 62/692,139, filed on Jun. 29, 2018, the entire disclosures of which are hereby incorporated by reference.

BACKGROUND

Field

The present specification generally relates to catalysts that efficiently convert various carbon-containing streams to $C_2$ and $C_3$ olefins. In particular, the present specification relates to preparation of hybrid catalysts and application of process methods to achieve a high conversion of synthesis gas feeds resulting in high and steady space-time yield of desired products. The synthesis gas comprises hydrogen gas and a carbon-containing gas selected from the group consisting of carbon monoxide, carbon dioxide, and mixtures thereof. A hybrid catalyst generally comprises a combination of a mixed metal oxide component and a molecular sieve that operate in tandem.

Technical Background

For a number of industrial applications, olefins are used, or are starting materials used, to produce plastics, fuels, and various downstream chemicals. These $C_2$ and $C_3$ materials may include ethylene and propylene. A variety of processes for producing these lower hydrocarbons has been developed, including petroleum cracking and various synthetic processes.

Synthetic processes for converting feed carbon to desired products, such as hydrocarbons, are known. Some of these synthetic processes begin with use of a hybrid catalyst. Different types of catalysts have also been explored, as well as different kinds of feed streams and proportions of feed stream components. However, many of these synthetic processes have low carbon conversion and much of the feed carbon does not get converted and exits the process in the same form as the feed carbon; the feed carbon is converted to $CO_2$; or these synthetic processes have low stability over time and the catalyst rapidly loses its activity for carbon conversion to desirable products.

Accordingly, a need exists for processes and systems that have a high conversion of feed carbon to desired products, such as, for example, $C_2$ and $C_3$ olefins in combination with a high stability of the catalyst.

SUMMARY

According to one embodiment, a hybrid catalyst comprises a metal oxide catalyst component comprising chromium, zinc, and at least one additional metal selected from the group consisting of aluminum and gallium; and a microporous catalyst component that is a molecular sieve having eight member ring (8-MR) pore openings. The metal oxide catalyst component comprises chromium and zinc with an atomic ratio of chromium:zinc (Cr:Zn) ranging from 0.35 to 1.00, and at least one (additional) metal selected from the group consisting of aluminum and gallium present in an amount from 25.0 at % to 40.0 atomic percent (at %).

In another embodiment, a process for preparing $C_2$ and $C_3$ olefins comprises: introducing a feed stream comprising hydrogen gas and a carbon-containing gas selected from the group consisting of carbon monoxide, carbon dioxide, and mixtures thereof into a reaction zone of a reactor; and converting the feed stream into a product stream comprising $C_2$ and $C_3$ olefins in the reaction zone in the presence of the hybrid catalyst. The hybrid catalyst comprises a mixed metal oxide catalyst component comprising metal elements chromium, zinc, and at least one (additional) metal selected from the group consisting of aluminum and gallium; and a microporous catalyst component that is a molecular sieve having 8-MR pore openings. The metal oxide catalyst component comprises chromium and zinc with an atomic ratio of chromium:zinc (Cr:Zn) from 0.35 to 1.00, and at least one additional metal present in an amount from 25.0 at % to 40.0 at %.

Additional features and advantages will be set forth in the detailed description which follows, and in part will be readily apparent to those skilled in the art from that description or recognized by practicing the embodiments described herein, including the detailed description which follows and the claims.

It is to be understood that both the foregoing general description and the following detailed description describe various embodiments and are intended to provide an overview or framework for understanding the nature and character of the claimed subject matter.

DETAILED DESCRIPTION

Reference will now be made in detail to embodiments of hybrid catalysts and methods using the hybrid catalyst to prepare $C_2$ and $C_3$ olefins. In one embodiment, a hybrid catalyst comprises a metal oxide catalyst component comprising chromium, zinc, and at least one additional metal selected from the group consisting of aluminum and gallium; and a microporous catalyst component that is a molecular sieve having 8-MR pore openings. The metal oxide catalyst component comprises chromium and zinc with an atomic ratio of chromium:zinc (Cr:Zn) from 0.35 to 1.00, and at least one additional metal present in an amount from 25.0 at % to 40.0 at %.

The use of hybrid catalysts to convert feed streams comprising carbon to desired products, such as, for example, $C_2$ and $C_3$ olefins, is known. However, many known hybrid catalysts are inefficient, because they exhibit a low feed carbon conversion and/or deactivate quickly as they are used, leading to a low space-time yield and low space-time yield stability for a given set of operating conditions over a given amount of time. In contrast, hybrid catalysts disclosed and described herein exhibit an improved space-time yield and space-time yield stability to $C_2$ and $C_3$ olefins. The composition of such hybrid catalysts used in embodiments is discussed below. As a summary, hybrid catalysts closely couple sequential reactions on each of the two independent catalysts. In the first step, a feed stream comprising hydrogen gas ($H_2$) and at least one of carbon monoxide (CO), carbon dioxide ($CO_2$), or a mixture of CO and $CO_2$, such as, for example, syngas, is converted into oxygenated hydrocarbons. In the second step, these oxygenates are converted into hydrocarbons (mostly short chain hydrocarbons, such as, for example $C_2$ and $C_3$ olefins). The continued withdrawal of oxygenates formed in the first step by the reactions of the second step ensures that there is no thermodynamic limit to achieve close to 100% (>99.9%) feed carbon conversion to hydrocarbons.

Hybrid catalyst systems comprise a metal oxide catalyst component, which converts the feed stream to oxygenated hydrocarbons, and a microporous catalyst component (such as, for example, a zeolite component), which converts the oxygenates to hydrocarbons. Known hybrid catalyst systems based on chromium-zinc metal oxide catalyst generally exhibit a trade-off between space-time yield and space-time yield stability to $C_2$ and $C_3$ olefins. There is therefore a need for a metal oxide catalyst component that results in a high space-time yield as well as a high space-time yield stability when combined with a microporous catalyst component in a hybrid catalyst process. It should be understood that, as used herein, the "metal oxide catalyst component" includes metals in various oxidation states. In some embodiments, the metal oxide catalyst component may comprise more than one metal oxide and individual metal oxides within the metal oxide catalyst component may have different oxidation states. Thus, the metal oxide catalyst component is not limited to comprising metal oxides with homogenous oxidation states.

Embodiments of hybrid catalysts and systems for using hybrid catalysts disclosed herein comprise a metal oxide catalyst component comprising: (1) chromium; (2) zinc; and (3) at least one (additional) metal in combination with a 8-MR microporous catalyst component, such as, for example, SAPO-34 molecular sieve. In embodiments, the additional metal is selected from the group consisting of gallium and aluminum. The hybrid catalysts disclosed and described herein convert feed streams to short chain olefins with higher space-time yield and higher space-time yield stability to $C_2$ and $C_3$ olefins than is commonly achieved with known chromium-zinc-oxide based hybrid mixtures. Thus, by using hybrid catalysts according to embodiments disclosed and described herein, a combination of high $C_2$ and $C_3$ olefin space-time yield and space-time yield stability over a given amount of time is achieved.

Metal oxide catalyst components for use in a hybrid catalyst according to embodiments will now be described. As referred to above, metals commonly used as constituents of the metal oxide catalyst component of some hybrid catalysts include combinations of zinc (Zn) and chromium (Cr). However, conventional hybrid catalysts comprising zinc and chromium do not have a combination of good space-time yield and good space-time yield stability when kept on stream for an extended period of time. Unexpectedly, it was found that adding aluminum (Al) or gallium (Ga) as an additional metal in the hybrid catalyst can result in a hybrid catalyst having good space-time yield and space-time yield stability. However, even with the addition of aluminum or gallium as an additional metal, the hybrid catalyst must also have the correct compositional ranges of metal oxides—Cr-, Zn-, and additional metal(s)—to yield good space-time yield and space-time yield stability. There is a relatively narrow compositional range of these metals that can be used in the metal oxide catalyst component of a hybrid catalyst that yields good space-time yield and good space-time yield stability. Without being bound by any particular theory, it is believed that the additional metal forms a spinel compound with zinc, which avoids segregation of zinc oxide that can be detrimental to $C_2$ and $C_3$ olefin production.

It was further unexpectedly found that the calcination temperature used to form the metal oxide catalyst component has a distinct effect on the desirable compositional range of the additional metal(s) that is/are added to the metal oxide catalyst component of the hybrid catalyst. For instance, a narrower range of additional metal(s) is, in embodiments, added to the metal oxide catalyst component when the metal oxide catalyst component is calcined at a temperature of greater than or equal to 500° C., and a broader range of additional metal(s) is, in embodiments, added to the metal oxide catalyst component when the metal oxide catalyst component is calcined at a temperature less than 500° C.

In embodiments disclosed herein, the composition of the metal oxide catalyst component is designated by an atomic percentage of its various metal constituents (i.e., Zn, Cr, and at least one additional metal selected from the group consisting of Al or Ga) based on the total amount of metals present in the metal oxide catalyst component (i.e., the sum of all metals in the metal oxide catalyst component equals 100%). In one or more embodiments, the composition of the metal oxide catalyst component is designated by atomic ratios of Cr:Zn as well as the atomic concentration (in atomic percent) of the additional metal—Al and/or Ga. Thus, 50% additional metal means that the additional metal(s) comprise(s) 50% of all metal atoms present in the metal oxide catalyst component. And, an atomic ratio of Cr:Zn means a ratio of Cr atoms to Zn atoms. As a non-limiting example, 25% Cr, 25% Zn, and 50% additional metal (such as, for example, Al or Ga) would mean that Cr comprises 25% of all metal atoms present in the metal oxide catalyst component, Zn comprises 25% of all metal atoms present in the metal oxide catalyst component, the additional metal comprises 50% of all metal atoms present in the metal oxide catalyst component, and a ratio of Cr:Zn is 1.00 (25%/25%). It should be understood that this percentage can also be referred to as at % herein.

A ratio of Cr:Zn is, in one or more embodiments, from 0.35 to 1.00, such as from 0.40 to 1.00, from 0.45 to 1.00, from 0.50 to 1.00, from 0.55 to 1.00, from 0.60 to 1.00, from 0.65 to 1.00, from 0.70 to 1.00, from 0.75 to 1.00, from 0.80 to 1.00, from 0.85 to 1.00, from 0.90 to 1.00, or from 0.95 to 1.00. In other embodiments, a ratio of Cr:Zn is from 0.35 to 0.95, such as from 0.35 to 0.90, from 0.35 to 0.85, from 0.35 to 0.80, from 0.35 to 0.75, from 0.35 to 0.70, from 0.35 to 0.65, from 0.35 to 0.60, from 0.35 to 0.55, from 0.35 to 0.50, from 0.35 to 0.45, or from 0.35 to 0.40. In yet other embodiments, a ratio of Cr:Zn is from 0.40 to 0.95, from 0.45 to 0.90, from 0.50 to 0.85, from 0.55 to 0.80, from 0.60 to 0.75, or from 0.65 to 0.70. In yet other embodiments, a ratio of Cr:Zn is from 0.35 to 0.90, such as from 0.35 to 0.50. When the ratio of Cr:Zn becomes too large, the space-time yield and/or space-time yield stability of the hybrid catalyst decreases.

According to one or more embodiments, a metal oxide catalyst component may be made by first forming an aqueous mixture of Cr-, Zn-, and additional metal-components. For example, in some embodiments, the Cr-, Zn-, and additional metal-components may be nitrates, such as chromium nitrate ($Cr(NO_3)_3$), zinc nitrate ($Zn(NO_3)_2$), aluminum nitrate ($Al(NO_3)_3$), and gallium nitrate ($Ga(NO_3)_3$). In other embodiments, the Cr-, Zn-, and additional metal-components used to prepare the catalyst may include any commonly known counter-ions such as, for example, acetates, formates, and the like, provided that the selected counter-ions decompose or combust at the calcination temperature to form oxides without leaving undesired residues. It should be understood that the amount of the Cr-, Zn-, and additional metal-containing components are selected such that the resulting metal oxide catalyst component will have values of the Cr:Zn ratio, and the amount of additional metal as defined and recited above.

In embodiments, a precipitating agent is prepared to be used to precipitate the Cr-, Zn-, and additional metal-component(s) from the above-referenced aqueous mixture. The precipitating agent, in one or more embodiments, is an aqueous mixture of a carbonate and/or hydroxide, such as, for example, ammonium carbonate (($NH_4$)$_2CO_3$), sodium carbonate ($Na_2CO_3$), sodium hydroxide (NaOH), or mixtures thereof. It should be understood that in embodiments other conventional precipitating agents may be used.

After the aqueous mixture of Cr-, Zn-, and additional metal-containing components and the precipitating agent are formulated, a precipitate is formed by adding these components to water maintained at a temperature from 40° C. to 80° C., such as from 45° C. to 65° C., or about 50° C. while mixing. In some embodiments, the aqueous mixture of Cr-, Zn-, and additional metal-containing component(s) and the precipitating agent are slowly added to the water so as to improve mixing of the components. The combination of the aqueous mixture of Cr-, Zn-, and additional metal-containing component(s) and the precipitating agent is maintained at a pH from 6.0 to 9.0, such as from 6.5 to 7.5, or from 7.0 to 7.5. The pH may be controlled by adjusting the ratio of the aqueous mixture of Cr-, Zn-, and additional metal-containing component(s) and precipitating agent that is added to the precipitating combination. This ratio may be adjusted by controlling the rate at which each component is added to the mixture. In some embodiments, the precipitate is aged in the mother liquor (i.e., the liquid in which the precipitate is formed) for a duration from 0.5 hours to 6.0 hours, such as from 1.0 hour to 5.0 hours, from 1.5 hours to 4.5 hours, from 2.0 hours to 4.0 hours, or from 2.5 hours to 3.5 hours.

The precipitate may be collected by conventional filtering, washing, and drying methods, or by other methods known to one of ordinary skill in the art. Once collected, the precipitate is calcined to form the metal oxide catalyst component that is used in a hybrid catalyst according to embodiments disclosed and described herein. The calcining process includes heating the precipitate to a temperature from 300 degrees Celsius (° C.) to 600° C. However, as noted above, the (acceptable/desirable) compositional range of the additional metal(s) that is/are added to the metal oxide catalyst component of the hybrid catalyst is affected by the temperature at which the precipitate is calcined. Therefore, in embodiments, the precipitate is calcined at temperatures less than 500° C., such as from 300° C. to less than 500° C., from 325° C. to less than 500° C., from 350° C. to less than 500° C., from 375° C. to less than 500° C., from 400° C. to less than 500° C., from 425° C. to less than 500° C., from 450° C. to less than 500° C., or from 475° C. to less than 500° C. In other embodiments, the precipitate is calcined at a temperature from 300° C. to 475° C., such as from 300° C. to 450° C., from 300° C. to 425° C., from 300° C. to 400° C., from 300° C. to 375° C., from 300° C. to 350° C., or from 300° C. to 325° C. In still other embodiments, the precipitate is calcined at temperatures of greater than or equal to 500° C. to 600° C., such as from 525° C. to 600° C., from 550° C. to 600° C., or from 575° C. to 600° C. In other embodiments, the precipitate is calcined at temperatures from greater than or equal to 500° C. to 575° C., such as from greater than or equal to 500° C. to 550° C., or from greater than or equal to 500° C. to 525° C. The duration of the calcination process may, in embodiments, be greater than or equal to 0.50 hours, such as greater than 1.00 hours, greater than 1.50 hours, greater than 2.00 hours, greater than 2.50 hours, greater than 3.00 hours, greater than 3.50 hours, greater than 4.00 hours, greater than 4.50 hours, or greater than 5.00 hours. In other embodiments, the duration of the calcining process may be from 0.50 hours to 8.00 hours, such as from 1.00 hours to 7.50 hours, from 1.50 hours to 7.00 hours, from 2.00 hours to 6.50 hours, from 2.50 hours to 6.00 hours, from 3.00 hours to 5.50 hours, from 3.50 hours to 5.00 hours, or from 4.00 hours to 4.50 hours. As disclosed above, the temperature at which the precipitate is calcined will determine the (acceptable/desirable) compositional range of the additional metal(s) that is/are added to the metal oxide catalyst component of the hybrid catalyst.

In embodiments where the precipitate is calcined at temperatures less than 500° C., the additional metal(s) is/are added to the metal oxide catalyst component of the hybrid catalyst in amounts from 25.0 atomic percent (at %) to 40 at %, such as from 27.5 at % to 40.0 at %, from 30.0 at % to 40.0 at %, from 32.5 at % to 40.0 at %, from 35.0 at % to 40.0 at %, or from 37.5 at % to 40.0 at %. In other embodiments where the precipitate is calcined at temperatures less than 500° C., the additional metal(s) is/are added to the metal oxide catalyst component of the hybrid catalyst in amounts from 25.0 at % to 39.0 at %, such as from 25.0 at % to 37.5 at %, from 25.0 at % to 35.0 at %, from 25.0 at % to 32.5 at %, from 25.0 at % to 30.0 at %, or from 25.0 at % to 27.5 at %. In still other embodiments, where the precipitate is calcined at temperatures less than 500° C., the additional metal(s) is/are added to the metal oxide catalyst component of the hybrid catalyst in amounts from 27.5 at % to 37.5 at %, such as from 30.0 at % to 35.0 at %, and in some embodiments from 27.0 at % to 35.0 at %.

In embodiments where the precipitate is calcined at temperatures greater than or equal to 500° C., the additional metal(s) is/are added to the metal oxide catalyst component of the hybrid catalyst in amounts from 25.0 at % to 35.0 at %, such as from 27.0 at % to 35.0 at %, from 29.0 at % to 35.0 at %, from 30.0 at % to 35.0 at %, from 32.0 at % to 35.0 at %, or from 34.0 at % to 35.0 at %. in other embodiments where the precipitate is calcined at temperatures greater than or equal to 500° C., the additional metal(s) is/are added to the metal oxide catalyst component of the hybrid catalyst in amounts from 25.0 at % to 33.0 at %, such as from 25.0 at % to 31.0 at %, from 25.0 at % to 30.0 at %, from 25.0 at % to 28.0 at %, or from 25.0 at % to 26.0 at %. In still other embodiments, where the precipitate is calcined at temperatures greater than or equal to 500° C., the additional metal(s) is/are added to the metal oxide catalyst component of the hybrid catalyst in amounts from 27.0 at % to 33.0 at %, such as from 29.0 at % to 31.0 at %.

In one or more embodiments, after the precipitate has been calcined to form the metal oxide catalyst component, it is physically mixed with a microporous catalyst component. The microporous catalyst component is, in embodiments, selected from molecular sieves having 8-MR pore openings and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the microporous catalyst component may be SAPO-34 silicoaluminophosphate having a Chabazite (CHA) framework type. Examples of these may include, but are not necessarily limited to: CHA embodiments selected from SAPO-34 and SSZ-13; and AEI embodiments such as SAPO-18. Combinations of microporous catalyst components having any of the above framework types may also be employed. It should be understood that the microporous catalyst component may have different membered ring pore opening depending on the desired product. For instance, microporous catalyst component having 8-MR to 12-MR pore openings could be used depending on the desired product. However, to produce $C_2$ and $C_3$ olefins, a microporous catalyst component having 8-MR pore openings is used in embodiments.

The metal oxide catalyst component and the microporous catalyst component of the hybrid catalyst may be mixed together by any suitable means, such as, for example, by physical mixing—such as shaking, stirring, or other agitation. The metal oxide catalyst component and the microporous catalyst component may be present in the reaction zone, typically as a hybrid catalyst in a catalyst bed, in a weight/weight (wt/wt) ratio (metal oxide catalyst component:microporous catalyst component) ranging from 0.1:1 to 10:1, such as from 0.5:1 to 9:1.

After the metal oxide catalyst component has been formed by a co-precipitation/calcination method and combined with a microporous catalyst component to form a hybrid catalyst, the hybrid catalyst may be used in methods for converting carbon in a carbon-containing feed stream to $C_2$ and $C_3$ olefins. Such processes will be described in more detail below.

In embodiments, the metal oxide catalyst component may be reduced within the reactor prior to exposure to the feed stream by exposing the metal oxide catalyst component to conventional reducing gases. In other embodiments, the metal oxide catalyst component may be reduced within the reactor upon exposure to reducing gases in the feed stream such as hydrogen and carbon monoxide.

According to embodiments, a feed stream is fed into a reaction zone, the feed stream comprising hydrogen ($H_2$) gas and a carbon-containing gas selected from carbon monoxide (CO), carbon dioxide ($CO_2$), and combinations thereof. In some embodiments, the $H_2$ gas is present in the feed stream in an amount of from 10 volume percent (vol %) to 90 vol %, based on combined volumes of the $H_2$ gas and the gas selected from CO, $CO_2$, and combinations thereof. The feed stream is contacted with a hybrid catalyst as disclosed and described herein in the reaction zone. The hybrid catalyst comprises a metal oxide catalyst component and a microporous catalyst component, wherein the metal oxide catalyst component comprises chromium, zinc, and at least one additional metal selected from the group consisting of aluminum and gallium. In some embodiments, the metal oxide catalyst component of the hybrid catalyst is a metal oxide catalyst component formed by the co-precipitation and calcination method described above. In certain embodiments, the microporous catalyst component is SAPO-34.

It should be understood that the activity of the hybrid catalyst will be higher for feed streams containing CO as the carbon-containing gas, and that the activity of the hybrid catalyst decreases as a larger portion of the carbon-containing gas in the feed stream is $CO_2$. However, that is not to say that the hybrid catalyst disclosed and described herein cannot be used in methods where the feed stream comprises $CO_2$ as all, or a large portion, of the carbon-containing gas.

The feed stream is contacted with the hybrid catalyst in the reaction zone under reaction conditions sufficient to form a product stream comprising $C_2$ and $C_3$ olefins. The reaction conditions comprise a temperature within reaction zone ranging, according to one or more embodiments, from 300° C. to 500° C., such as from 300° C. to 475° C., from 300° C. to 450° C., from 300° C. to 425° C., from 300° C. to 400° C., from 300° C. to 375° C., from 300° C. to 350° C., or from 300° C. to 325° C. In other embodiments, the temperature within the reaction zone is from 325° C. to 500° C., from 350° C. to 500° C., from 375° C. to 500° C., from 400° C. to 500° C., from 425° C. to 500° C., from 450° C. to 500° C., or from 475° C. to 500° C. In yet other embodiments, the temperature within the reaction zone is from 300° C. to 500° C., such as from 325° C. to 475° C., from 350° C. to 450° C., or from 375° C. to 425° C.

The reaction conditions also, in embodiments, include a pressure inside the reaction zone of at least 5 bar (500 kilopascals (kPa)), such as at least 10 bar (1,000 kPa), at least 15 bar (1,500 kPa), at least 20 bar (2,000 kPa), or at least 25 bar (2,500 kPa). In other embodiments, the reaction conditions include a pressure inside the reaction zone from 10 bar (1,000 kPa) to 30 bar (3,000 kPa), such as from 15 bar (1,500 kPa) to 25 bar (2,500 kPa), or about 20 bar (2,000 kPa).

Benefits of catalysts disclosed and described herein are an increase in space-time yield (STY) and STY stability. To calculate the STY, reactor effluent composition is obtained by gas chromatography and the conversion and carbon based selectivities are calculated using the following equations:

$$X_{CO}(\%) = [\eta_{CO,in} - \eta_{CO,out}]/\eta_{CO,in} \cdot 100; \text{ and} \quad (1)$$

$$S_j(\%) = [\alpha_j \cdot \eta_{j,out}/(\eta_{CO,in} - \eta_{CO,out})] \cdot 100, \quad (2)$$

where $X_{CO}$ is defined as the CO conversion (%), $\eta_{CO,\,in}$ is defined as the molar inlet flow of CO (μmol/s), $\mu_{CO,\,out}$ is the molar outlet flow of CO (μmol/s), $S_j$ is defined as the carbon based selectivity to product j (%), $\alpha_j$ the number of carbon atoms for product j, $\eta_{j,\,out}$ is the molar outlet flow of product j (μmol/s).

The STY of CO to $C_2$ and $C_3$ olefins (μmol C/cm³ cat/s) is calculated by the following equation:

$$STY_{C2-C3=} = \frac{\eta_{CO,in} * X_{CO} * S_{C2-C3=}}{10000 * V_{cat}}, \quad (3)$$

where, $S_{C2-C3=}$ is defined as the carbon based selectivity to $C_2$ and $C_3$ olefins, and $V_{cat}$ is defined as the volume of metal oxide catalyst component in cm³. The stability in STY is defined as the slope in $C_2$ and $C_3$ olefin STY as a function of time. It is measured by fitting a linear curve to the $C_2$ and $C_3$ olefin STY as function of time, from the time on stream where the slope of the linear curve is approximately constant (after the initial catalyst break in). It should be understood that a skilled artisan is capable of determining the appropriate time on stream starting point of the linear fit to the STY as a function of time on stream.

As mentioned above, the combined space-time yield and space-time yield stability to olefins of the hybrid catalysts disclosed and described herein is greater than the combined space-time yield and space-time yield stability to olefins of the heretofore known hybrid catalysts.

It should be understood that the STY and stability in STY can vary based upon e.g., feed rates of the various components and catalyst loading within the reactor. Thus, when hybrid catalysts are compared using STY, the STY for each of the catalysts to be compared should be calculated at the same process parameters and conditions. In this way, an accurate comparison of the catalysts can be made.

EXAMPLES

Embodiments will be further clarified by the following examples.

Examples 1-6 and Comparative Examples 1-8

Chromium-zinc-additional metal catalysts were prepared by the co-precipitation method. Stoichiometric amounts of $Cr(NO_3)_3 \cdot 9H_2O$, $Zn(NO_3)_2 \cdot 6H_2O$ and $M(NO_3)_3 \cdot xH_2O$, where M is the additional metal (i.e., $(Al(NO_3)_3 \cdot 9H_2O$, or $Ga(NO_3)_3 \cdot 9H_2O$) were added to distilled water ($H_2O$), targeting a total metal concentration of 1 mol/L and metal molar ratios as shown in Table 1. In addition, an aqueous 2 M solution of $(NH_4)_2CO_3$ was prepared as a precipitating agent. The metal nitrate and precipitating agent solutions were simultaneously added dropwise to a stirred round bottom flask containing 200 mL distilled $H_2O$ maintained at pH=7 and T=50° C. The co-precipitated materials were filtered, washed with distilled water, dried in static air at 85° C. overnight, and subsequently calcined at 400 or 600° C.—as indicated in Table 1—for 2 h. The obtained catalysts had an atomic Cr:Zn:M ratio as specified in Table 1.

For the catalytic testing, 150 μL of Chromium-Zinc-M catalyst was physically mixed with 150 μL of a silicoaluminophosphate catalyst (SAPO-34) by shaking them together in a bottle. Each of the catalysts had a particle size before mixing within a range of from 40 mesh (0.422 millimeter) to 80 mesh (0.178 millimeter). Prior to contacting with syngas, the catalyst was heated under nitrogen ($N_2$) to reaction temperature and pressure. Catalytic performance test was carried out at 20 bar (2.0 MPa), 390° C. by flowing 6 ml/min of a syngas mixture (60% $H_2$, 30% CO and 10% He) over the catalyst placed in a 3 mm stainless steel reactor tube. The reactor effluent composition was obtained by gas chromatography and the STY and STY stability were calculated using the equations above. The results of the catalytic testing are shown in Table 1 below.

TABLE 1

| Example | Additional Metal (M) | Cr:Zn:M (at %) | Calcination Temperature (° C.) | STY $C_2$ and $C_3$ olefins (μmol C/cm³ cat/s) at 90 h TOS | STY Slope $C_2$ and $C_3$ olefins (μmol C/cm³ cat/s/hr)$^a$ |
|---|---|---|---|---|---|
| Ex. 1 | Al | 23:45:32 | 400 | 1.027 | −8.78E−4 |
| Ex. 2 | Al | 23:45:32 | 600 | 1.079 | −1.00E−3 |
| Ex. 3 | Al | 34:38:28 | 400 | 1.121 | −3.14E−5 |
| Ex. 4 | Ga | 22:51:27 | 400 | 1.027 | +1.30E−4 |
| Ex. 5 | Ga | 22:51:27 | 600 | 1.001 | −1.29E−3 |
| Ex. 6 | Ga | 17:44:39 | 400 | 0.966 | −9.62E−4 |
| Comp. Ex. 1 | None | 29:71:0 | 400 | 0.543 | −3.24E−3 |
| Comp. Ex. 2 | None | 29:71:0 | 600 | 0.540 | −2.45E−3 |
| Comp. Ex. 3 | Al | 23:55:22 | 400 | 0.621 | −2.45E−4 |
| Comp. Ex. 4 | None | 50:50:0 | 400 | 0.812 | −2.06E−4 |
| Comp. Ex. 5 | None | 50:50:0 | 600 | 0.483 | −1.23E−4 |
| Comp. Ex. 6 | Al | 38:31:31 | 400 | 0.634 | +3.05E−4 |
| Comp. Ex. 7 | Al | 38:31:31 | 600 | 0.493 | −2.50E−5 |
| Comp. Ex. 8 | Ga | 17:44:39 | 600 | 0.765 | −3.34E−3 |

*TOS is time on stream.
$^a$Fitted from data at steady-state condition (TOS > 70 h)

As can be seen in Table 1, Examples 1-6 all had an STY of at least 0.82 μmol/cm³ cat/s and a decay in STY—as identified by the STY slope—of less than an absolute value of 1.50 E−3. From this data, it was observed that the addition of aluminum or gallium as an additional metal in a chromium-zinc based metal oxide catalyst component can, when added in the correct ratios, increase the olefin space-time yield in combination with an increased space-time yield stability over time as compared to conventional chromium-zinc metal oxide catalyst components.

Comparative Examples 9-12

Chromium-Zinc-M catalysts were prepared by the co-precipitation method as described in Examples 1-6 and Comparative Examples 1-8.

For catalytic test, 200 μl of Chromium-Zinc(-M) catalyst was physically mixed with 200 μL of a silicoaluminophosphate catalyst (SAPO-34) by shaking them together in a bottle. Each of the catalysts had a particle size before mixing within a range of from 60 mesh (0.250 millimeter) to 80 mesh (0.178 millimeter). Prior to contacting with syngas, the catalyst was heated under $N_2$ to reaction temperature and pressure. Catalytic performance test was carried out at 20 bar (2.0 MPa), 395° C. by flowing 8 ml/min of a syngas mixture (60% $H_2$, 30% CO and 10% He) over the catalyst placed in 2 mm quartz reactor tube. The reactor effluent composition was obtained by gas chromatography and the STY and STY stability were calculated using the equations above. The compositions and catalytic testing results are shown below in Table 2.

TABLE 2

| Example | Additional Metal (M) | Cr:Zn:M (at %) | Calcination Temperature (° C.) | STY $C_2$ and $C_3$ olefins (μmol C/cm³ cat/s) 90 h TOS | STY Slope $C_2$ and $C_3$ olefins (μmol C/cm³ cat/s/hr) |
|---|---|---|---|---|---|
| Comp. Ex. 9 | None | 29:71:0 | 400 | 0.841 | −4.54E−3 |
| Comp. Ex. 10 | Al | 22:56:22 | 400 | 1.302 | −4.78E−3 |
| Comp. Ex. 11 | None | 50:50:0 | 400 | 1.561 | −3.05E−3 |
| Comp. Ex. 12 | None | 41:59:0 | 400 | 1.607 | −4.18E−3 |

*TOS is time on stream

A comparison of Comparative Example 10 to Comparative Examples 9, 11, and 12 shows that adding an additional metal (i.e., aluminum) in amounts outside of the ranges disclosed and described herein does not provide any increase in stability when compared to a chromium-zinc catalyst without an additional metal, which highlights the importance of the compositional ranges of catalysts disclosed and described herein.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A process for preparing $C_2$ and $C_3$ olefins comprising:
    introducing a feed stream comprising hydrogen gas and a carbon-containing gas selected from the group consisting of carbon monoxide, carbon dioxide, and mixtures thereof into a reaction zone of a reactor; and
    converting the feed stream into a product stream comprising $C_2$ and $C_3$ olefins in the reaction zone in the presence of a hybrid catalyst, wherein the hybrid catalyst comprises:
    a metal oxide catalyst component comprising chromium, zinc, and at least one additional metal selected from the group consisting of aluminum and gallium; and a SAPO-34 microporous catalyst component, wherein
an atomic ratio of chromium:zinc (Cr:Zn) is from 0.35 to 1.00, and
the at least one additional metal is present in an amount from 25.0 at % to 40.0 at %.

2. The process of claim 1, wherein the at least one additional metal is aluminum.

3. The process of claim 2, wherein the atomic ratio of chromium to zinc is from 0.35 to 0.90.

4. The process of claim 2, wherein the metal oxide catalyst component is calcined at a temperature less than 500° C.

5. The process of claim 1, wherein the at least one additional metal is gallium.

6. The process of claim 5, wherein the atomic ratio of chromium to zinc is from 0.35 to 0.90.

7. The process of claim 5, wherein the metal oxide catalyst component is calcined at a temperature less than 500° C.

8. The process of claim 1, wherein the atomic ratio of chromium to zinc is from 0.35 to 0.90.

9. The process of claim 1, wherein the metal oxide catalyst component is calcined at a temperature less than 500° C.

10. The process of claim 9, wherein the metal oxide catalyst component is calcined at temperatures from 300° C. to less than 500° C.

11. The process of claim 9, wherein the at least one additional metal is present in an amount from 25.0 at % to 39.0 at %.

12. The process of claim 9, wherein the atomic ratio of chromium to zinc is from 0.35 to 0.50.

13. The process of claim 1, wherein the metal oxide catalyst component is calcined at temperatures greater than or equal to 500° C.

14. The process of claim 13, wherein the metal oxide catalyst component is calcined at temperatures from 500° C. to 600° C.

15. The process of claim 14, wherein the at least one additional metal is present in an amount from 25.0 at % to 35.0 at %.

16. The process of claim 14, wherein the atomic ratio of chromium to zinc is from 0.35 to 0.5.

17. The process of claim 13, wherein the at least one additional metal is present in an amount from 25.0 at % to 35.0 at %.

18. The process of claim 13, wherein the atomic ratio of chromium to zinc is from 0.35 to 0.5.

* * * * *